United States Patent
Camus et al.

(10) Patent No.: US 7,577,471 B2
(45) Date of Patent: Aug. 18, 2009

(54) OPTICAL COHERENCE TOMOGRAPHY SYSTEM

(75) Inventors: Estelle Camus, Erlangen (DE); Oliver Meissner, München (DE); Thomas Redel, Poxdorf (DE)

(73) Assignee: Siemens Aktiengesellschaft, Munich (DE)

( * ) Notice: Subject to any disclaimer, the term of this patent is extended or adjusted under 35 U.S.C. 154(b) by 308 days.

(21) Appl. No.: 11/523,395

(22) Filed: Sep. 19, 2006

(65) Prior Publication Data

US 2007/0065080 A1   Mar. 22, 2007

(30) Foreign Application Priority Data

Sep. 21, 2005   (DE) ................ 10 2005 045 088

(51) Int. Cl.
    *A61B 5/05*   (2006.01)
(52) U.S. Cl. .............. 600/407; 385/115; 385/116; 600/160; 600/129; 606/11; 606/12; 356/336; 356/481
(58) Field of Classification Search ........... 600/160, 600/129, 407, 476–478; 606/11, 12; 356/336, 356/481; 385/115, 116
    See application file for complete search history.

(56) References Cited

U.S. PATENT DOCUMENTS 6,546,272 B1   4/2003   MacKinnon et al.

FOREIGN PATENT DOCUMENTS

EP   0 330 376 A2   8/1989
EP   0 581 871 B1   2/1994

OTHER PUBLICATIONS

S.H. Yun, G.J. Tearney, B.E. Bouma, B.H. Park, and J.F. De Boer; "High-Speed spectral-domain optical coherence tomography at 1.3 μm wavelenght"; Optics Express, Dec. 29, 2003, pp. 3598-3604, vol. 11, No. 26.
James G. Fujimoto; "Optical coherence tomography for ultrahigh resolution in vivo imaging"; Nature Biotechnology; Nov. 2003; pp. 1361-1367; vol. 21, No. 11.

*Primary Examiner*—Brian Casler
*Assistant Examiner*—Joel M Lamprecht

(57) ABSTRACT

An optical coherence tomography system includes a catheter in which is arranged a plurality of light conducting fibers. It further includes a plurality of optical units. Light from the proximal end to the distal end and signals from the distal end to the proximal end can be transmitted simultaneously in different fibers. Time is saved through the simultaneous signal processing of signals from different fibers. That is advantageous particularly in the imaging, by means of coherence tomography, of blood vessels that have to be occluded for said imaging.

16 Claims, 3 Drawing Sheets

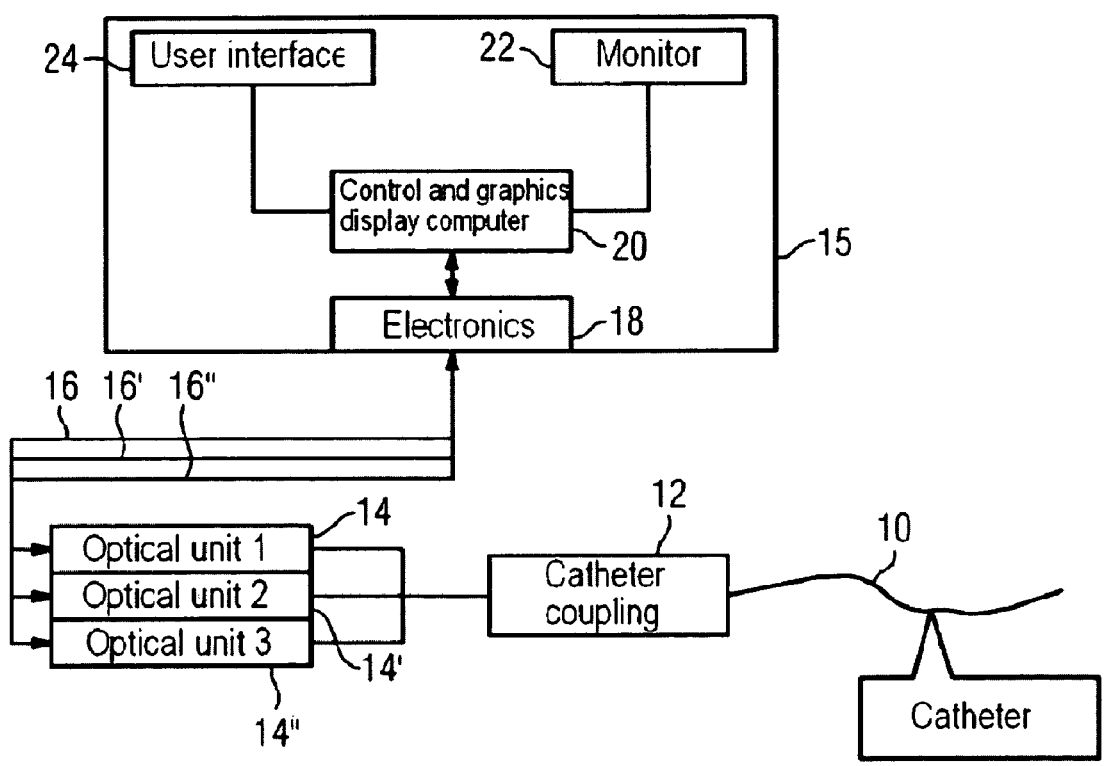

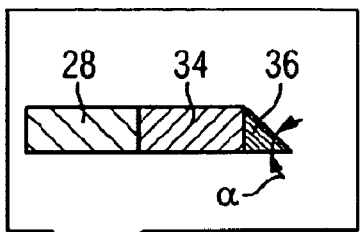
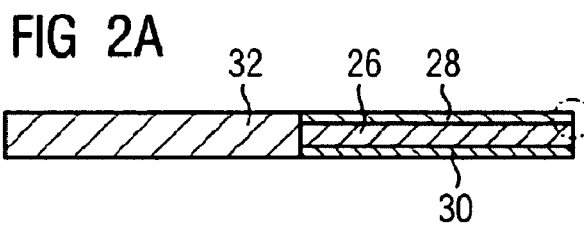
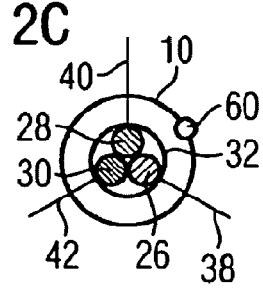
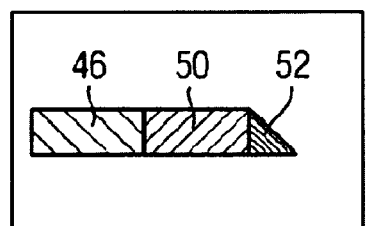
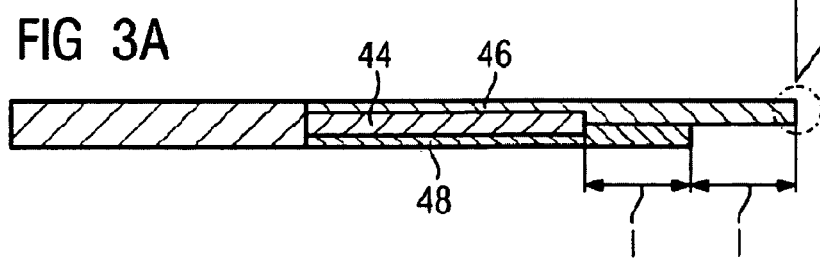
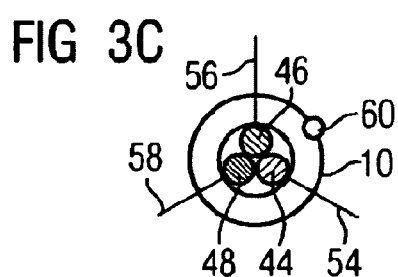
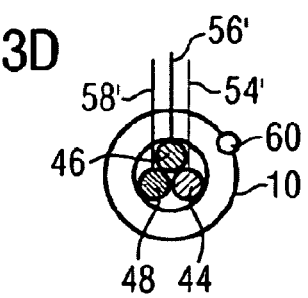

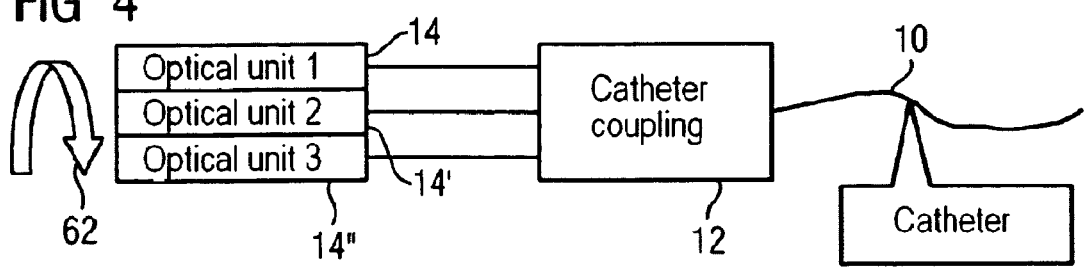
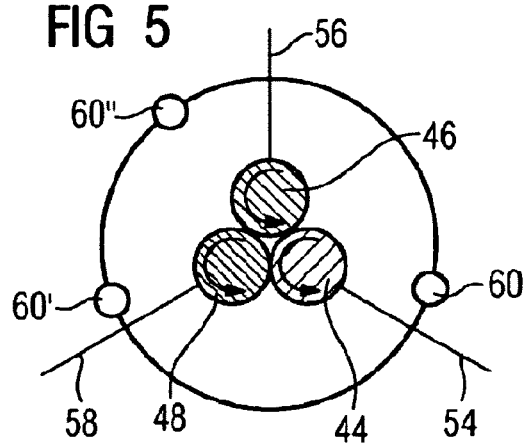
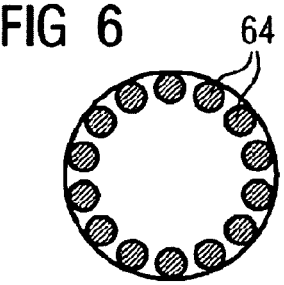
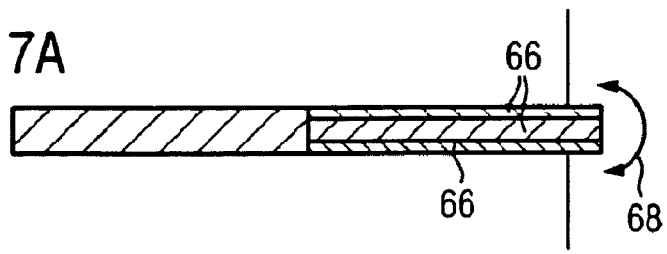
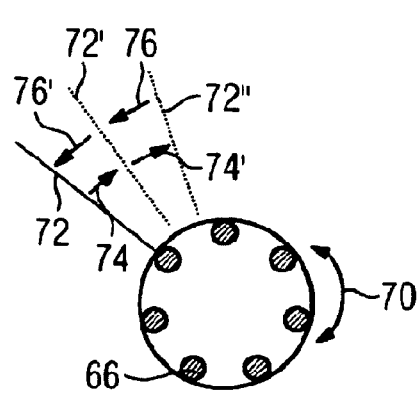

OPTICAL COHERENCE TOMOGRAPHY SYSTEM

CROSS REFERENCE TO RELATED APPLICATIONS

This application claims priority of German application No. 10 2005 045 088.1 filed Sep. 21, 2005, which is incorporated by reference herein in its entirety.

FIELD OF THE INVENTION

The invention relates to an optical coherence tomography system having a catheter arranged with a plurality of light conducting fibers.

BACKGROUND OF THE INVENTION

Optical coherence tomography is still a very new imaging technology. An outline of optical coherence tomography is given in, for example, the article "Optical coherence tomography for ultrahigh resolution in vivo imaging" by James G. Fujimoto, in "Nature Biotechnology", Volume 21, Number 11, November 2003, pp. 1361 ff. Variations are described in European patent EP 0 581 871 B1.

Not only the surface of a sample is imaged in optical coherence tomography; in-depth imaging also takes place. While in the case of ultrasound systems a relevant signal can be assigned to a depth on the basis of certain differences in signal propagation time, in optical systems it is necessary to operate with interferometry, with the depth of the sample being examined, for example a tissue, then corresponding in terms of magnitude to the wavelength of the radiation employed.

Optical coherence tomography, which is a particularly advanced technology, enables intracorporal lumina to be imaged. For this purpose, a catheter is introduced into the body being examined. While EP 0 581 871 B1 describes an embodiment in which a bundle of fibers is provided in a catheter, with the individual fibers being addressed sequentially during scanning and not simultaneously, the present invention proceeds from an embodiment in which basically only one fiber is needed for producing a full cross-sectional image of an intracorporal lumen. Part of said fiber is therein a lens located on the distal end and a deflector unit. Light is then beamed through the fiber via the lens and the deflector unit onto the wall of the intracorporal lumen and reflected back therefrom. The reflected light is guided back through the fiber and taken to an evaluating process at the proximal end of the fiber. The cited interferometry is introduced by arranging a Michelson interferometer in front of the proximal fiber end, with the interferometer unit including a beam splitter and a reference path, with half the split beam being guided into the reference path. Said beam portion is reflected back there and traverses the reference path in the opposite direction in order to be overlaid with the signal that is decoupled from the fiber's proximal end. The thus overlaid signal is taken to an evaluation unit consisting essentially of a detector in the interferometry unit. The detector signal is taken to a signal processing system, which is to say to a computer and, where applicable, upstream electronic components. To produce a complete image, the catheter is then turned along with the fiber. The lens consequently turns along with the deflector element and the beam exiting the fiber at the distal end will be guided in another direction in keeping with the turn. Another part of the vessel wall of the lumen being imaged is irradiated analogously.

The turn is assigned in the signal evaluation unit to the signal obtained in this way so a complete two-dimensional image will result when the fiber is turned through 360°. Because different depths of the tissue of the lumen being examined are scanned simultaneously, said images will correspond to a cross-sectional image that was obtained at the height of the distal end of the fiber and provides information about the examined lumen perpendicular to the axis of rotation.

It is generally desirable for a three-dimensional data record to be generated. A plurality of said cross-sectional images must therefore be recorded at different heights of the intracorporal lumen. Because the light beam exits the fiber in a defined manner, the fiber must for this purpose be moved in the lumen. It can be moved after a cross-sectional image has been recorded, meaning after turning has taken place, so that a sequence of cross-sectional images is obtained; but it can also be moved continuously during turning, with the signals then obtained constituting a real three-dimensional data record for which the lumen was scanned spirally. The fiber is as a rule moved not forward but back. Typical speeds of retraction are around 0.5 mm/s to 2 mm/s.

What is problematic is that when blood vessels are shown in cross-sectional images the blood will disrupt the representation. Emitted light, typically having a wavelength of 1,300 nanometers, is mainly scattered by the blood's constituents. That is why in the prior art the blood is briefly kept away for image recording. That can be done by flushing the entire blood vessel with a cell-free fluid while the image is being recorded without occluding the blood flow. Another possibility is to occlude the blood flow by means of a balloon on a catheter (known from, for instance, EP 0 330 376 A2). Occluding customarily takes place upstream of the imaging site, with a little fluid being flushed into the vessel downstream so that the vessel remains cell-free and a good image quality is achieved.

At the above-mentioned speed of retraction, in the case of a three-dimensional representation of a blood vessel the problem thus arises that if a 10-centimeter length has to be represented the vessel will have to remain sealed for at least 50 seconds. That is a relatively long period for a live system.

SUMMARY OF THE INVENTION

The object of the invention is to provide an optical coherence tomography system with the aid of which three-dimensional image data records of blood vessels or of the kind of lumina where recording of brief duration is advantageous can be produced significantly faster than in the prior art.

To achieve said object the invention proposes an optical coherence tomography system having the features of the claims.

An optical coherence tomography system of said type thus includes a catheter in which are arranged a plurality of light conducting fibers and a plurality of optical units each assigned to one fiber. Said optical units are assigned and embodied in such a way that light from the respectively assigned unit in the individual fibers can be guided independently of the other fibers from a proximal fiber end to a distal fiber end and, analogously, a (response) signal can be guided from the distal fiber end to the proximal fiber end in each fiber independently of the other fibers and can be independently evaluated in the respectively assigned optical unit (or, as the case may be, prepared for evaluation). The optical units' mutual independence is in particular such that light and signals can be transmitted in different fibers simultaneously. The individual fibers can inventively be turned together with the associated optical unit independently of the other fibers.

The optical coherence tomography system claimed thus provides a plurality of autonomous subsystems consisting of fibers and optical units, with each optical unit being embodied such as to enable an optical coherence tomography image or image portions to be obtained. Each optical unit has in particular an interferometer unit having a reference arm and an evaluation unit having a detector.

Because a plurality of signals can be obtained simultaneously and the fibers can be controlled mutually independently, the time needed to record images having a specific number of image elements is inversely proportional to the number of light conducting fibers and optical units. If, say, three independent fibers are used along with three optical units assigned thereto, then it will be possible in each case to record three signals simultaneously and thus reduce the length of time to record a cross-sectional image to one third or to produce three such cross-sectional images simultaneously, depending on the position of the fibers.

Notwithstanding the optical units' independence it is possible to provide a single light source for a plurality of optical units in common. Independent controlling of the plurality of light conducting fibers will be possible then, too. A saving in components is achieved thereby, and it will not be necessary actually to combine a plurality of independent coherence tomography systems; instead, independence will be required in partial systems only, such as the optical units and light conducting fibers, while a common catheter and common light source are provided.

A single signal processing unit can likewise be provided in common, with the same advantages being gained.

Said embodiment is further advantageous especially because a single image can be obtained from signals from at least two different fibers. It is advantageous with said embodiment for the distal ends of at least two different fibers to be provided at the same height in the catheter. Different areas of the blood vessel wall will then in each case be scanned when the fibers are turned mutually independently. The signals obtained are assembled into a cross-sectional image.

It is alternatively and additionally possible to produce an entire series of images in the signal processing unit, with the individual images in said series each being obtained from signals from a partial number of the fibers. Said individual images in the series are therein preferably obtained from individual fibers. Said embodiment can advantageously be realized by providing the distal ends of at least two different fibers spatially displaced along a catheter axis in the catheter.

Signals from two different height areas of the vessel being examined will hence be obtained when the two fibers are turned and signals are recorded independently, which thus obtained signals can in each case be used on completion of a full 360° turn for obtaining a cross-sectional image. In keeping with the distal ends' spatial displacement, two cross-sectional images will then be obtained that together form part of the series of images.

While signals for the individual images are generated twice as fast in the embodiment in which the distal ends of at least two different fibers are provided at the same height in the catheter area, meaning that the fibers can be moved twice as fast in the vessel being imaged, in the embodiment in which the distal ends of at least two different fibers are provided spatially displaced in the catheter, two or more cross-sectional images are recorded simultaneously but, each taken individually, just as fast as when only one fiber is used as in the prior art. The spatial displacement is advantageously selected such as to subdivide typical lengths of the fiber's movement in the vessel. So if the spatial displacement is selected appropriately, the individual fibers will have to be moved along only a partial length, for example three fibers will have to be moved along only one third of the total length, with said moving continuing until the distal end of the first fiber reaches the place where the distal end of the second fiber was previously located. If the distal ends are arranged equidistantly, the distal end of the second fiber will at that time reach the site at which the third fiber was previously located and the third fiber will then reach the end of the length over which the image is produced.

The individual fibers are in a preferred embodiment each surrounded by a separate casing. All fibers can alternatively or additionally be surrounded by a common casing.

Said casing is beneficial particularly when the fibers are turned and moved longitudinally as it will fundamentally make it easier to move the fibers.

In a preferred embodiment, each optical unit can be turned. That takes account of the invention's fundamentally proceeding from the fact that imaging takes place through turning the fibers. In the case of optical units that can be turned, the link between the optical units and the fibers can be fixed and a transition from a turning to a fixed system has to be provided only at the interface to the signal processing unit, for example at the detector's signal output.

It will be of beneficial use for obtaining a three-dimensional data record if on or in the catheter an optical marking is provided that is discernible on the image. Said optical marking will make it possible to subsequently detect both the fiber's position from the image as well as, where applicable, the fiber's longitudinal movement. In a sensitive system, such as one comprising a plurality of fibers, a particular possible occurrence is for the fibers' mutual spatial relationship to change slightly. The optical marking will therein assist the signal processing unit in automatically correcting possible movements and displacements so that a reliable three-dimensional data record can be computed.

Instead of a separate optical marking, the imaging of the catheter as such, which is basically discernible on the image, can also be used in spatially assigning signals to each other. An optical marking is advantageous compared to the catheter faintly visible on the image on account only of the strength of the signal produced by said marking.

BRIEF DESCRIPTION OF THE DRAWINGS

Preferred embodiments of the invention will now be described with reference to the drawing.

FIG. 1 is a schematic of the components of an optical coherence tomography system;

FIG. 2A being a general view of the fibers,

FIG. 2B being a partial view of the tip of a fiber, and

FIG. 2C being a plan view of what is shown in FIG. 2A from the right;

FIG. 3A being a general view of the three fibers,

FIG. 3B being a partial view of the tip of a fiber; and

FIGS. 3C and 3D are each plan views of the embodiment shown in FIG. 3A from the right that correspond to different versions of beam scanning in this alternative;

FIG. 4 is a schematic illustration of the ability of the totality of optical units to be turned;

FIG. 5 is a schematic illustration of the ability of individual fibers to be turned mutually independently;

FIG. 6 shows an embodiment having a larger number of independent fibers;

FIG. 7A is a general view of an embodiment having a plurality of fibers showing the movement for signal generating, and FIG. 7B are a cross-section through what is shown in FIG. 7A.

DETAILED DESCRIPTION OF THE INVENTION

FIG. 1 shows the overall system employed for the invention.

The invention employs a single catheter 10. Located in said catheter 10 are three light conducting fibers (not shown in FIG. 1, but see FIG. 2 and FIG. 3). Each individual fiber is linked via a catheter coupling 12 to an associated optical unit. Shown in the figure are the optical unit 1, designated 14, that is linked to the first fiber, the optical unit 2, designated 14', that is linked to the second fiber, and the optical unit 3, designated 14", that is linked to the third fiber via the catheter coupling 12. The optical units 14, 14', and 14" are herein optical units conforming to the prior art for optical coherence tomography systems, which is to say Michelson interferometer units having a reference arm and an evaluation facility that includes, for example, a detector. The optical units 14, 14,' and 14" are independent to the effect that the individual fibers in the catheter 10 can receive light mutually independently and that each send back signals to the optical units 14, 14', and 14" mutually independently so that each individual fiber can be used independently of the other fibers for obtaining signals, doing so simultaneously with the obtaining of signals with the assistance of the other two fibers.

A single operator system 15 can be provided if the mutual independence of the optical units 14, 14', and 14" has been insured. The optical units 14, 14', and 14" are each controlled via separate control leads 16, 16', and 16", which leads or, as the case may be, leads parallel thereto (not shown) are also used for routing signals selected by the detector back to a system comprising upstream electronics 18 and a control and graphics display computer 20, which is to say to a signal processing unit. Said common signal processing unit 20 is customarily linked to a monitor 22 and a user interface 24.

Two alternatives are presented here for the fiber arrangement.

FIG. 2A shows the first alternative. The fibers 26, 28, and 30 are arranged alongside each other and are surrounded by a common casing 32. At the tip, each individual fiber 26, 28, and 30 appears as shown by way of example in FIG. 2B for the fiber 28. The distal end of the fiber 28 ends in a lens 34, shown here schematically, which focuses the light onto a deflector unit 36, likewise shown schematically. The angle a through which the deflector unit 36 is tilted is preferably 45° so that a light beam exiting the fiber 28 will radiate away from the fiber at an angle of 90°. That is illustrated in FIG. 2C. The fiber 26 has herein been assigned the light beam 38, the fiber 28 the light beam 40, and the fiber 30 the light beam 42. Not shown in FIG. 2C is the wall of a vessel being imaged, for example a blood vessel, from which wall the light radiating perpendicularly back on the same path as the light beams 38, 40, and 42 is recoupled into the fibers 26, 28 or, as the case may be, 30 and is used for signal generating in the optical units 14, 14', and 14".

The embodiment shown in FIG. 2A has the advantage that three light beams 38, 40, and 42 simultaneously scan the surroundings of the distal end of the fibers 26, 28, and 30 so that each fiber or the entire system has to be turned by a third in order to obtain a complete cross-sectional image from the signals obtained. Because only a third of a turn is necessary, imaging is three times faster than in the prior art where only a single fiber is used.

An alternative is shown in FIG. 3A. The distal ends of three fibers, 44, 46, and 48 are therein arranged spatially mutually displaced, with the distance between the end of the first fiber 44 and second fiber 48 on the one hand and the second fiber 48 and third fiber 46 on the other being in each case l. The tips of the fibers 44, 46, and 48 herein again appear the same as shown schematically in FIG. 3B for the fiber 46: A lens 50 is arranged on the fiber 46, and in front of said lens is a deflector unit 52.

The distances l have presently been selected in such a way that a typical vessel section being imaged is 3l long. The light beams exiting the fibers 44, 46, and 48 are mutually independent: A complete rotation of the respective fiber 44, 46, and 48 must be performed at each of the heights, defined by the distal ends of the fibers 44, 46, and 48, of the vessel being imaged. It is thus irrelevant whether the light beams exit the fibers 44, 46, and 48 simultaneously as light beams 54, 56, and 58, as shown in FIG. 3C, at a mutual angle of 120° or whether all light beams 54', 56' and 58', as shown in FIG. 3D, point in the same direction and are radiated out in parallel even when the fibers are turned relative to each other.

In the embodiments shown in FIG. 2C, FIG. 3C, and FIG. 3D, an optical marking 60 can be provided on the catheter 10. One of the light beams 38, 40, and 42 (FIG. 2C) or all light beams 54, 54', 56, 56' and 58, 58' (FIG. 3C and FIG. 3D) will scan the optical marking 60 when the individual fibers are turned. The optical marking 60 will produce a corresponding signal on the cross-sectional image in the embodiment according to FIG. 2C or, as the case may be, on the cross-sectional images in the embodiment according to FIG. 3C and FIG 3D. The optical marking 60 makes it possible to determine the light beam's spatial orientation, in particular its angle. If the optical marking in the case of the embodiment is also perpendicular to the presentation plane according to FIG. 3C and FIG. 3D so that its form is characteristic, it will also be possible to ascertain the distal position of the fiber ends of the fibers 44, 46, and 48 from the imaged optical marking 60E.

It has already been mentioned that the individual fibers have to be turned during imaging. It can herein be advantageous to turn the individual fibers together. That applies both to the embodiment according to FIG. 2A, FIG. 2B, FIG. 2C and to the embodiment according to FIG. 3A, FIG. 3B, FIG. 3C, and FIG. 3D. The casing 32 herein holds, by way of example, the fibers 26, 28, and 30 together.

FIG. 4 shows a section of the system according to FIG. 1 and, by means of the arrow 62, illustrates that not only the individual fibers 26, 28, and 30 or also 44, 46, and 48 turn together but that the corresponding optical units 14, 14', and 14" can likewise be turned together. The catheter coupling 12 can accordingly be relatively rigid while, for example, sliding contacts can be provided at the transition into the leads 16, 16', and 16" (not shown in FIG. 4, though illustrated in FIG. 1) so that electrical contact will also be insured during turning.

FIG. 5 illustrates another embodiment for which, analogously to FIGS. 2C and 3C and FIG. 3D, a plan view of the embodiment is shown where the individual fibers can be turned mutually independently. Said embodiment is advantageous especially when the alternative according to FIG. 3C is selected, which is to say when the fibers 44, 46, and 48 are provided having mutually displaced distal ends. Although it is not in every case insured that the light beams 54, 56, and 58 from the respectively other fibers will not be adversely affected in their travel, virtually complete scanning through 360° is in any event possible. To facilitate evaluation, a further optical marking element 60' can be provided in addition to the one optical marking element 60, or yet a further optical marking element 60".

In the embodiment according to FIG. 5 it is advantageous for each of the fibers 44, 46, and 48 to have an individual casing to make them easier to move mutually independently. A common casing of the type shown in FIG. 2A, namely casing 32, is, though, additionally possible but not necessary.

The embodiments shown hitherto utilize three fibers. The overall system is as a result three times as fast as in the prior art where only one fiber is used. That will as a rule provide sufficient time for imaging a blood vessel that has to be occluded.

Should, though, more speed be required, then more than two or three fibers can be provided, for example, as shown in FIG. 6, fourteen fibers 64. Virtually no turning will be necessary in a system of that type.

It will already cease being necessary to provide turning in the case of a system, illustrated in FIG. 7, having seven fibers 66. Illustrated in FIG. 7A is the overall representation of a fiber system that has been introduced into a catheter and comprises seven fibers 66 that can be counted in the plan view shown in FIG. 7B. It will suffice, as indicated by the arrow 68, simply to swing the entire system back and forth. When the system is being swung back and forth according to arrow 68 or, as the case may be, arrow 70 in the representation perpendicular hereto, a light beam 72 will scan according to the swing, as indicated by the arrow 74 or, as the case may be, 74', in the light beam exiting directions 72 and 72" indicated by the dotted lines. When the system is swung back according to the arrow 68 or, as the case may be, 70, the light beam will move from the position 72" according to the arrow 76 or, as the case may be, 76' across the position 72' back to the position 72. Because all seven fibers 66 each emit light beams analogous to the light beam 72, which is swung through a specific area, the entire 360° area will ultimately be scanned. A signal processing unit is able, using the control signals for the swinging mechanism, to assign to the swing the reflection signals guided back over the fibers 66 and accordingly produce cross-sectional images of the vessel being examined.

As regards the number of independent fibers it must be observed that a compromise has to be found here between a moderately large number of three fibers, as shown FIGS. 2 and 3, and a very large number of fourteen fibers 64, as shown in FIG. 6. Attention is drawn to a separate optical unit's having to be provided for each fiber, which unit includes in particular an interferometer unit. The number 14, as indicated in FIG. 6, must hence rather be regarded as too high because the Michelson interferometers on the proximal end of the catheter (or, as the case may be, on the catheter coupling (12)) will impede each other. As illustrated in FIG. 7, a medium number of independent systems having independent fibers 66 (and seven independent optical units) will suffice to render turning superfluous. The exact number of fibers used will depend on the requirements placed on imaging that are determined in particular by the image recording time available.

The invention claimed is:

1. An optical coherence tomography system, comprising:
    a catheter;
    a plurality of light conducting fibers arranged on the catheter; and
    a plurality of optical units each assigned to one of the fibers respectively, wherein each optical unit comprises an interferometer unit which comprises a reference arm and an evaluation unit having a detector, and wherein a single light source is provided for the optical units,
    wherein the optical units are configured such that:
        light from the each assigned optical unit in the respective fiber is guided from a proximal fiber end to a distal fiber end independently of other fibers, and
        a signal is guided from the distal fiber end to the proximal fiber end independently of other fibers and independently evaluated in the respectively assigned optical unit so that the light and the signal are transmitted simultaneously in different fibers,
    wherein each fiber is configured to turn together with the associated optical unit independently of other fibers.

2. The optical coherence tomography system as claimed in claim 1, wherein a single signal processing unit is provided which guides signals from the optical units.

3. The optical coherence tomography system as claimed in claim 2, wherein the signal processing unit obtains an image from signals from at least two different fibers.

4. The optical coherence tomography system as claimed in claim 2, wherein a series of images is processed in the signal processing unit with each image obtained from a portion of the fibers.

5. The optical coherence tomography system as claimed in claim 4, wherein the portion of the fibers is an individual fiber.

6. The optical coherence tomography system as claimed in claim 1, wherein distal ends of at least two different fibers are provided at a same height in the catheter.

7. The optical coherence tomography system as claimed in claim 1, wherein distal ends of at least two different fibers are spatially displaced along a catheter axis of the catheter.

8. The optical coherence tomography system as claimed in claim 1, wherein each of the fiber is surrounded by a separate casing.

9. The optical coherence tomography system as claimed in claim 1, wherein the fibers are surrounded by a common casing.

10. The optical coherence tomography system as claimed in claim 1, wherein each of the optical units is turned individually.

11. The optical coherence tomography system as claimed in claim 1, wherein the fibers are turned in common along with associated optical units while maintaining a relative mutual spatial relationship.

12. The optical coherence tomography system as claimed in claim 1, wherein an optical marking is provided on the catheter which enables signals from different fibers spatially assigned to each other.

13. The optical coherence tomography system as claimed in claim 1, wherein the signal is guided from the distal fiber end to the proximal fiber end independently of other fibers and independently prepared to be evaluated in the respectively assigned optical unit.

14. A method for an optical coherence tomography system having a catheter, comprising:
    arranging a plurality of light conducting fibers on the catheter;
    providing a plurality of optical units, each unit comprising a reference arm and an evaluation unit having a detector;
    assigning the plurality of optical units each to one of the fibers respectively;
    guiding light from the each assigned optical unit in the respective fiber from a proximal fiber end to a distal fiber end independently of other fibers;
    guiding a signal from the distal fiber end to the proximal fiber end independently of other fibers;
    evaluating the signal in the respectively assigned optical unit independently;

turning each fiber together with the associated optical unit independently of other fibers; and transmitting the light and the signal simultaneously in different fibers.

15. The method as claimed in claim 14, wherein each of the optical units is turned individually.

16. The method as claimed in claim 14, wherein the fibers are turned in common along with associated optical units while maintaining a relative mutual spatial relationship.

* * * * *